United States Patent [19]

O'Byrne

[11] Patent Number: 5,037,385
[45] Date of Patent: Aug. 6, 1991

[54] CONTINUOUS AMBULATORY PERITONEAL DIALYSIS METHOD

[75] Inventor: Paul O'Byrne, Dublin, Ireland

[73] Assignee: National Research Development Corporation, London, England

[21] Appl. No.: 424,165

[22] Filed: Oct. 23, 1989

[30] Foreign Application Priority Data

Oct. 24, 1988 [GB] United Kingdom ............... 8824855

[51] Int. Cl.$^5$ ............................................. A61M 5/00
[52] U.S. Cl. ........................................ 604/28; 604/29; 604/43
[58] Field of Search ................. 604/4, 8, 9, 27-31, 604/43

[56] References Cited

U.S. PATENT DOCUMENTS

| | | | |
|---|---|---|---|
| 3,707,967 | 1/1973 | Kitrilakis et al. | 604/29 |
| 4,261,341 | 4/1981 | Hakim et al. | 128/1 R |
| 4,416,657 | 11/1983 | Berglund | 604/9 |
| 4,490,137 | 12/1984 | Moukheibir | 604/28 |
| 4,681,560 | 7/1987 | Schulte et al. | 604/8 X |
| 4,850,955 | 7/1989 | Newkirk | 604/8 X |

FOREIGN PATENT DOCUMENTS

| | | |
|---|---|---|
| 0270205 | 6/1988 | European Pat. Off. |
| 2390940 | 12/1978 | France . |
| 2458287 | 6/1981 | France . |
| 2224939A | 5/1990 | United Kingdom . |

*Primary Examiner*—C. Fred Rosenbaum
*Assistant Examiner*—Corrine Maglione
*Attorney, Agent, or Firm*—Nixon & Vanderhye

[57] ABSTRACT

A wholly implantable continuous ambulatory peritoneal dialysis system comprises a first part (20) including tubing (21) for location as an access catheter affording a flowpath for dialysing solution from a subcutaneous portal, accessible by percutaneous needle, to the peritoneal cavity (11), and a second part (30) including a pump (33) and a further tubing (31, 32) serially interconnectable for location as a shunt affording a flowpath for the solution, following dialysis, from the cavity to the bladder (12), the pump being operable under control by the patient (10) to effect the shunt flow.

5 Claims, 1 Drawing Sheet

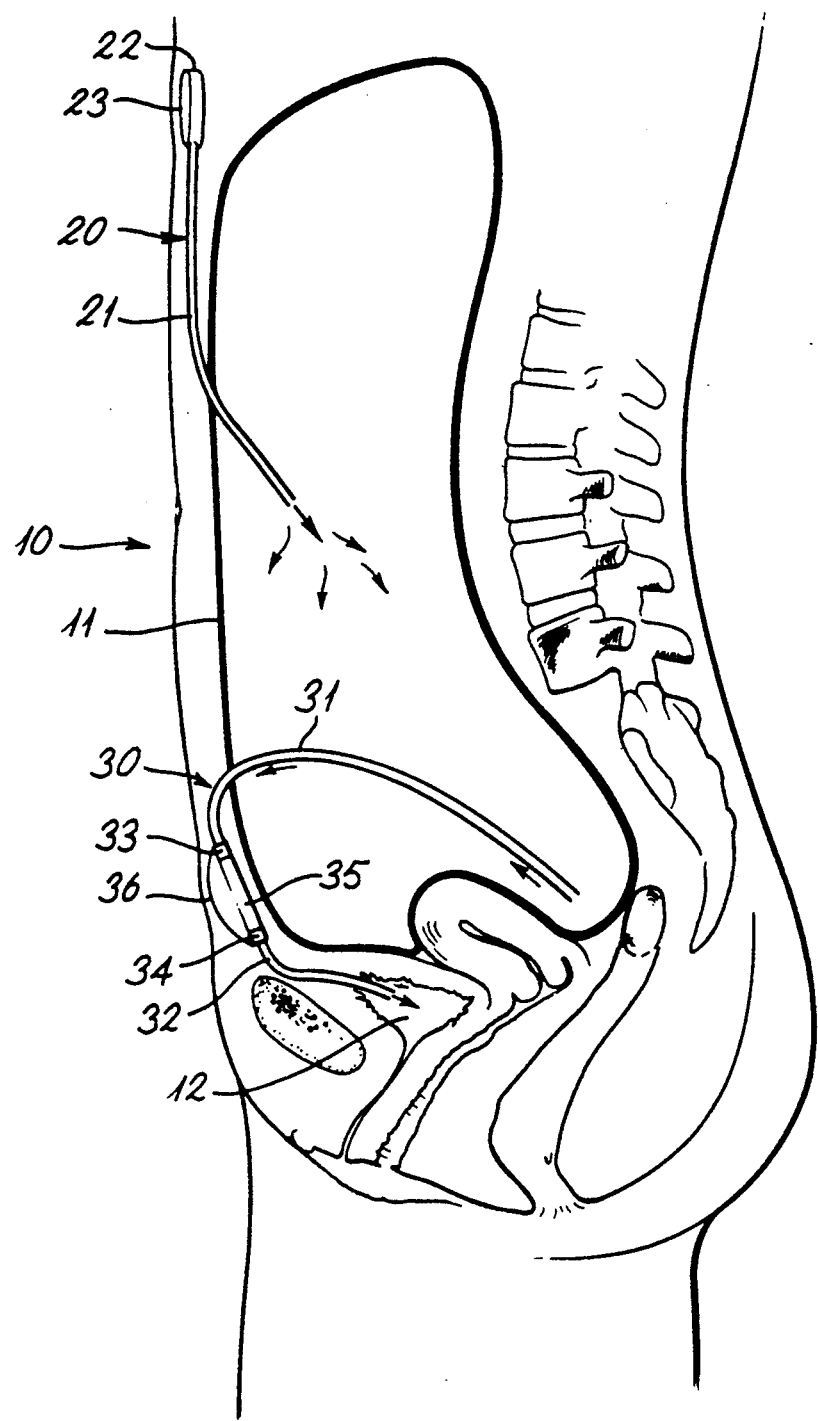

5,037,385

CONTINUOUS AMBULATORY PERITONEAL DIALYSIS METHOD

This invention concerns dialysis whereby, in the absence of an adequate natural renal function, a different mechanism is used to effect mass exchange between a body fluid and another solution. Typically this mechanism effects the desired exchange by osmosis through a semi-permeable or microporous membrane separating the fluid and solution, with the exchange extracting from the fluid components of an accumulatively toxic or other undesirable nature and possibly at the same time adding from the solution other desirable components.

Conventionally such a mechanism is of an extra-corporeal form communicated by tubing with appropriate vessels of the body, but this is disadvantageous in a variety of ways. It involves immobilization of a patient for the lengthy period that is necessary for a useful degree of exchange to occur, and such an exchange is commonly required at intervals of only a few days to sustain life. Also it is expensive of resources in terms of equipment and operative personnel.

Attempts have been made to simplify and compact equipment for this conventional approach whereby it is more economic and portable with the patient to allow ambulatory usage, or at least facilitate domestic usage. However, it is difficult to say that these objectives have been satisfactorily attained.

More recently it has been proposed that these last objectives be better attained by an approach referred to as Continuous Ambulatory Peritoneal Dialysis or CAPD whereby the lining of the peritoneum is used as the dialysis membrane. In this approach an appropriate solution is to be fed under gravity from a suitably elevated reservoir by way of a catheter into the peritoneal cavity, the solution being left in place for dialysis to occur through the membrane, and the solution thereafter being drained under gravity by way of a catheter to a vessel at low elevation. This is clearly economic in terms of equipment and a patient has greater mobility in that immobility is only required for the purposes of solution feeding and draining.

However, CAPD as so far proposed is still subject to disadvantage. The patient is subject to immobilization for inconvenient periods of up to the order of 20 minutes each for solution feeding and draining, and also the catheter tubing must be accommodated by wrapping around the body in some way. More seriously, because drainage is effected directly from the peritoneal cavity, the bladder ceases to perform its natural function and is liable to shrinkage and this, in turn, is potentially problematical in relation to a subsequently successful renal transplant and an associated requirement for renewed normal bladder function. More serious still is the effectively inevitable incidence of peritonitis through infection by way of the transcutaneous track of the catheter or by endoluminal contamination. Experience indicates infection to be a serious risk in various procedures involving catheters or the like in non-transient usage, and such a risk is additionally high with CAPD because the solution fed to the peritoneal cavity will be at abnormal PH. volume and osmotic pressure and so act to reduce normal immune system activity.

An object of the present invention is to provide a basis for improved CAPD whereby the above disadvantages are significantly reduced.

SUMMARY OF THE INVENTION

To this end it is proposed that a wholly implantable CAPD system be provided, the system comprising a first part including tubing for location as an access catheter affording a flow path for dialysing solution from a subcutaneous portal, accessible by percutaneous needle, to the peritoneal cavity, and a second part including a pump and further tubing serially interconnectable for location as a shunt affording a flow path for the solution, following dialysis, from the cavity to the bladder, with the pump being operable under recipient control.

Preferably the catheter has a relatively enlarged hollow structure at one end of the associated tubing, which structure is closed by a self-sealing septum for penetration by the needle, the solution being applied by way of the needle and catheter for installation in the peritoneal cavity. This structure is preferably to be located at a subcutaneous site below a denervated tissue flap to avoid pain through repeated injection Such a site will normally be located at the lower costal margin to provide a rigid background for the access procedure.

In the second part the pump preferably comprises a chamber of variable volume having two ports connectable with separate portions of further tubing, and two unidirectional valves respectively operably connected with the ports to allow flow into and out of the chamber. Such a pump is operable alternately to compact and expand the chamber volume respectively to cause fluid outflow and inflow.

In one form such a pump chamber has a resiliently deformable wall of domed or other appropriate shape for siting to allow transcutaneous manual operation to compress the chamber, with expansion occurring by resilient action. As an alternative the pump can have a bellows or other collapsible/expansible form for siting between adjacent muscles which act by contraction and relaxation to operate the pump. Siting in the suprapubic space is suitable for the first of these pump forms, with the recti muscles being associated in the other form.

The valves for these pumps are suitably of slit form to maintain simplicity in the overall structure of the system.

The benefits of the presently proposed system are largely self-evident relative to the prior CAPD system as described above. The patient's quality of life is significantly improved in terms of convenience by way of the complete system implantation and pumped drainage with a return to normal micturition. Also bladder function is sustained to improve a possible subsequent transplant situation. The risk of peritonitis is at least greatly reduced by complete implantation of the system. In addition, any incidence of infection arising in the system will be conveyed to the bladder and can activate the immune system in a normal manner.

BRIEF DESCRIPTION OF THE DRAWINGS

For further clarification of the invention by way of example, a presently preferred embodiment thereof is diagrammatically illustrated in situ in a patient in the accompanying drawing.

DETAILED DESCRIPTION OF THE INVENTION

In the drawing the patient is denoted at 10.

The first part 20 of the implanted system comprises an access catheter tube 21 connected at one end for communication with the interior of a relatively enlarged hollow terminal structure 22 closed by a self-sealing septum 23. This one end is located subcutaneously below a denervated tissue flap at the lower costal margin with the septum facing outwardly of the patient for access by a percutaneous needle. The other end of the tube 21 is located in the peritoneal cavity 11.

The second part 30 of the implanted system comprises two lengths of shunt tubing 31,32 and a pump 35 serially connected between them. The tube/pump connections are made by way of respective ones of two ports in the pump, which ports house individual unidirectional valves 34,33 of slit form orientated in mutually opposite senses relative to the pump to act as inflow and outflow valves. The pump is in the simple form of a chamber having a resiliently deformable domed wall 36 operable by compression to cause fluid outflow, with resilient expansion thereafter causing fluid inflow. The tube 31 is connected with inflow valve 33 and has its free end located in the cavity 11, the pump is located subcutaneously in the suprapubic space for manual operation by the patient, and the free end of tube 32 is located in the bladder 12.

While the invention has been described with reference to presently preferred forms and usage, variation is possible. For example other forms of pump are possible, including powered forms with activation by way of an implanted power source such as biogalvanic cell form, say, or with activation transcutaneously such as by induction from an extracorporeal source, say. Also, other forms of valve can be used, such as flap, cuspidate leaflet or ball valves, for example.

Also, in use, the fluid input end of the first shunt, and the pump, can have different locations than those specifically indicated above.

I claim:

1. The method of surgically applying an apparatus as a continuous ambulatory peritoneal dialysis system in a patient, which apparatus comprises:
   a first part including a length of tubing; and
   a second part including a pump operable under the control of the patient, and a further length of tubing; and
   which method comprises:
   wholly implanting the first part tubing with one end located at a subcutaneous site accessible by percutaneous needle and the other end in the peritoneal cavity to serve as an access catheter affording a flow path for dialysing solution administered by way of said needle; and
   wholly implanting said second part pump and further tubing in serial interconnection with one end located in said cavity and the other end located in the bladder to serve as a shunt affording a flow path for said solution, following dialysis, from the cavity to the bladder.

2. A method according to claim 1, wherein said pump is resiliently deformable, and said pump is implanted at a site to allow subsequent pump operation by manual action effected transcutaneously.

3. A method according to claim 2, wherein said site is the suprapubic space.

4. A method according to claim 1, wherein said pump is of a collapsible/expansible form, and said pump is implanted at a site between adjacent muscles to allow subsequent pump operation by contraction and relaxation of said muscles.

5. A method according to claim 4, wherein said site is the recti muscles.

* * * * *